(12) United States Patent
Chodkowski et al.

(10) Patent No.: US 12,017,004 B2
(45) Date of Patent: Jun. 25, 2024

(54) DUAL SLIDER HEADGEAR ADJUSTMENT SYSTEM WITH EASY PULL TABS AND PATIENT INTERFACE DEVICE INCLUDING SAME

(71) Applicant: KONINKLIJKE PHILIPS N.V., Eindhoven (NL)

(72) Inventors: Lauren Patricia Chodkowski, Pittsburgh, PA (US); Evan Lawrence, Monroeville, PA (US); Anna Dzuricky, Erie, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 680 days.

(21) Appl. No.: 17/110,376

(22) Filed: Dec. 3, 2020

(65) Prior Publication Data

US 2021/0178102 A1 Jun. 17, 2021

Related U.S. Application Data

(60) Provisional application No. 62/948,895, filed on Dec. 17, 2019.

(51) Int. Cl.
*A61M 16/06* (2006.01)

(52) U.S. Cl.
CPC .... *A61M 16/0683* (2013.01); *A61M 16/0644* (2014.02); *A61M 16/0672* (2014.02)

(58) Field of Classification Search
CPC .... A61M 16/0683; A61M 16/06–0694; A62B 18/02; A62B 18/025; A62B 18/08; A62B 18/084; A62B 23/02; A62B 23/025
See application file for complete search history.

(56) References Cited

U.S. PATENT DOCUMENTS

| 9,517,320 | B2 * | 12/2016 | Barlow | A61M 16/0057 |
| 2003/0196656 | A1 * | 10/2003 | Moore | A61M 16/0622 128/201.22 |
| 2003/0196662 | A1 * | 10/2003 | Ging | A61M 16/0066 128/204.15 |
| 2004/0182398 | A1 * | 9/2004 | Sprinkle | A61M 16/0638 128/207.13 |
| 2010/0283956 | A1 | 11/2010 | Jackson et al. | |

(Continued)

FOREIGN PATENT DOCUMENTS

EP 2060294 A1 5/2009

*Primary Examiner* — Valerie L Woodward
(74) *Attorney, Agent, or Firm* — Michael W. Haas (57) ABSTRACT

An adjustment system includes: a first strap assembly and a second strap assembly positioned 180 degrees with respect to, and entwined with, the first strap assembly. Each strap assembly includes a slider having first and second slots therein. The slots are defined, in-part, by a central portion extending between both of the slots, a first end portion extending along the first slot opposite the central portion, and a second end portion extending along the second slot opposite the central portion. Each strap assembly further includes a strap portion having a first end coupled to the second end portion of the slider and an opposite second end structured to be coupled to one or more of the patient interface device or another portion of the headgear; and a tab coupled to the first end portion of the slider, the tab being structured to be grasped by the patient.

10 Claims, 5 Drawing Sheets

(56) References Cited

U.S. PATENT DOCUMENTS

2012/0067349 A1\* 3/2012 Barlow ............ A61M 16/0075
128/205.25
2014/0201950 A1 7/2014 Girault et al.
2017/0021121 A1 1/2017 Cameron et al.

\* cited by examiner

DUAL SLIDER HEADGEAR ADJUSTMENT SYSTEM WITH EASY PULL TABS AND PATIENT INTERFACE DEVICE INCLUDING SAME

CROSS-REFERENCE TO RELATED APPLICATIONS

This patent application claims the priority benefit under 35 U.S.C. § 119(e) of U.S. Provisional Application No. 62/948,895 filed on Dec. 17, 2019, the contents of which are herein incorporated by reference.

BACKGROUND OF THE INVENTION

1. Field of the Invention

The present invention pertains to headgear for use in securing patient interface devices to the head of a patient and, more particularly, to adjustment systems for use in adjusting such headgear to fit the head of a patient. The present invention further pertains to strap assemblies for use in such adjustment systems.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the pressure support device with the airway of the patient, so that a flow of breathing gas can be delivered from the pressure/flow generating device to the airway of the patient.

The patient interface device is typically secured to the patient's head by a headgear component. Headgear components typically include one or more straps that wrap partially, or completely around the back of the patient's head. Hook and loop fastening arrangements are commonly used to provide for adjustability of headgear components, however such arrangements limit material selection and typically require use of a lamination. An alternative approach is the use of elastic materials in headgear to provide for deformation of the headgear when installing or removing from the patient's head, however such arrangements tend to stretch out over time and do not offer true adjustability. Some sliding adjustment arrangements are known, however, such arrangements are typically difficult to adjust or generally only adjustable in a single direction. Accordingly, there is room for improvement in adjustment systems for use in headgear for securing patient interface devices to the head of a patient.

SUMMARY OF THE INVENTION

As one aspect of the invention, an adjustment system for use in a headgear for securing a patient interface device to the head of a patient is provided. The adjustment system comprises: a first strap assembly; and a second strap assembly positioned 180 degrees with respect to the first assembly and entwined with the first strap assembly. Each of the first strap assembly and the second strap assembly comprises: a slider having a body comprising: a first slot defined in the body; and a second slot defined in the body parallel to the first slot, wherein the first slot and the second slot are each defined in-part by an elongate central portion of the body that is disposed between, and extends along the length of both the first slot and the second slot, wherein the first slot is further defined by an elongate first end portion of the body that extends along the length of the first slot and is disposed parallel to the central portion, wherein the second slot is further defined by an elongate second end portion of the body that extends along the length of the second slot and is disposed parallel to the central portion on the opposite side thereof from the first end portion, wherein the central portion, the first end portion, and the second end portion are coupled together at a top end of the body and at a bottom end of the body via other portions of the body, thus forming the first slot and the second slot; a strap portion having a first end coupled to the second end portion of the slider and an opposite second end structured to be coupled to one or more of the patient interface device or another portion of the headgear; and a tab coupled to the first end portion of the slider, the tab being structured to be grasped by the patient.

The tab of each of the first strap assembly and the second strap assembly may comprise an opening defined therein.

In each of the first strap assembly and the second strap assembly, the tab may be coupled to the first end portion of the slider by an end portion of the tab that: extends through the first slot of the slider, is folded around the first end portion of the body back onto an adjacent part of the tab, and is secured to the adjacent portion of the tab.

In each of the first strap assembly and the second strap assembly, the tab may be coupled to the slider via over-molding of a portion of the tab over a portion of the slider.

In each of the first strap assembly and the second strap assembly the tab and the slider may be formed as portions of a single unitary member.

In each of the first strap assembly and the second strap assembly the slider may be coupled to the tab via over-molding of a portion of the slider over a portion of the tab and over-molding of another portion of the slider over a portion of the strap portion.

The first strap assembly and the second strap assembly may be entwined such that: the strap portion of the first strap assembly extends from slider of the first strap assembly, along the strap portion of the second strap assembly before passing in front of the second end portion of the slider of the second strap assembly; the strap portion of the first strap assembly then passes rearward through the second slot of the slider of the second strap assembly, wraps partially around the central portion of the slider of the second strap assembly, and then passes forward through first slot of the slider of the second strap assembly; the strap portion of the first strap assembly then passes in front of the first end portion of the slider of the second strap assembly, passes rearward through the opening of the tab of the second strap assembly, and then extends to an end structured to be coupled with the one or more of the patient interface device or another portion of the headgear; the strap portion of the second strap assembly extends from the slider of the second strap assembly, along the strap portion of the first strap assembly before passing behind the second end portion of the slider of the first strap assembly; the strap portion of the second strap assembly then passes forward through the second slot of the slider of the first strap assembly, wraps partially around the central portion of the slider of the first strap assembly, and then passes rearward through the first slot of the slider of the first strap assembly; and the strap portion of the second strap assembly then passes behind the first end portion of the slider of the first strap assembly, behind the tab of the first strap assembly without passing through the opening of the first strap assembly, and then extends to another end structured to be coupled with the one or more of the patient interface device or another portion of the headgear.

As another aspect of the invention, a respiratory interface system for providing a regimen of respiratory therapy to a patient comprises: a patient interface device that is structured to communicate a flow of breathing gas received to an airway of the patient; and a headgear coupled to the patient interface device, the headgear being structured to secure the patient interface device to the head of the patient, the headgear including an adjustment system such as described herein.

As yet a further aspect of the invention, a strap assembly for an adjustment system for use in a headgear for securing a patient interface device to the head of a patient is provided. The strap assembly comprises: a slider having a body comprising: a first slot defined in the body; and a second slot defined in the body parallel to the first slot, wherein the slot and the second slot are each defined in-part by an elongate central portion of the body that is disposed between, and extends along the length of both the first slot and the second slot, wherein the first slot is further defined by an elongate first end portion of the body that extends along the length of the first slot and is disposed parallel to the central portion, wherein the second slot is further defined by an elongate second end portion of the body that extends along the length of the second slot and is disposed parallel to the central portion on the opposite side thereof from the first end portion, wherein the central portion, the first end portion, and the second end portion are coupled together at a top end of the body and at a bottom end of the body via other portions of the body, thus forming the first slot and the second slot; a strap portion having a first end coupled to the second end portion of the slider and an opposite second end structured to be coupled to one or more of the patient interface device or another portion of the headgear; and a tab coupled to the first end portion of the slider, the tab being structured to be grasped by the patient.

The tab may comprise an opening defined therein.

The tab may be coupled to the first end portion of the slider by one of: an end portion of the tab that: extends through the first slot of the slider, is folded around the first end portion of the body back onto an adjacent part of the tab, and is secured to the adjacent portion of the tab; or via over-molding of a portion of the tab over a portion of the slider.

The tab and the slider may be formed as portions of a single unitary member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the statement that two or more parts or components "engage" one another shall means that the parts exert a force against one another either directly or through one or more intermediate parts or components.

As used herein, the word "unitary" means a component is created as a single piece or unit. That is, a component that includes pieces that are created separately and then coupled together as a unit is not a "unitary" component or body.

As used herein, the term "number" shall mean one or an integer greater than one (i.e., a plurality).

As used herein, a "coupling assembly" includes two or more couplings or coupling components. The components of a coupling or coupling assembly are generally not part of the same element or other component. As such the components of a "coupling assembly" may not be described at the same time in the following description.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together or "snuggly correspond." In that situation, the difference between the size of the components is even smaller whereby the amount of friction increases. If the element defining the opening and/or the component inserted into the opening is/are made from a deformable or compressible material, the opening may even be slightly smaller than the component being inserted into the opening. This definition is further modified if the two components are said to "substantially correspond." "Substantially correspond" means that the size of the opening is very close to the size of the element inserted therein. That is, not so close as to cause substantial friction, as with a snug fit, but with more contact and friction than a "corresponding fit," i.e. a "slightly larger" fit.

Figure 1:
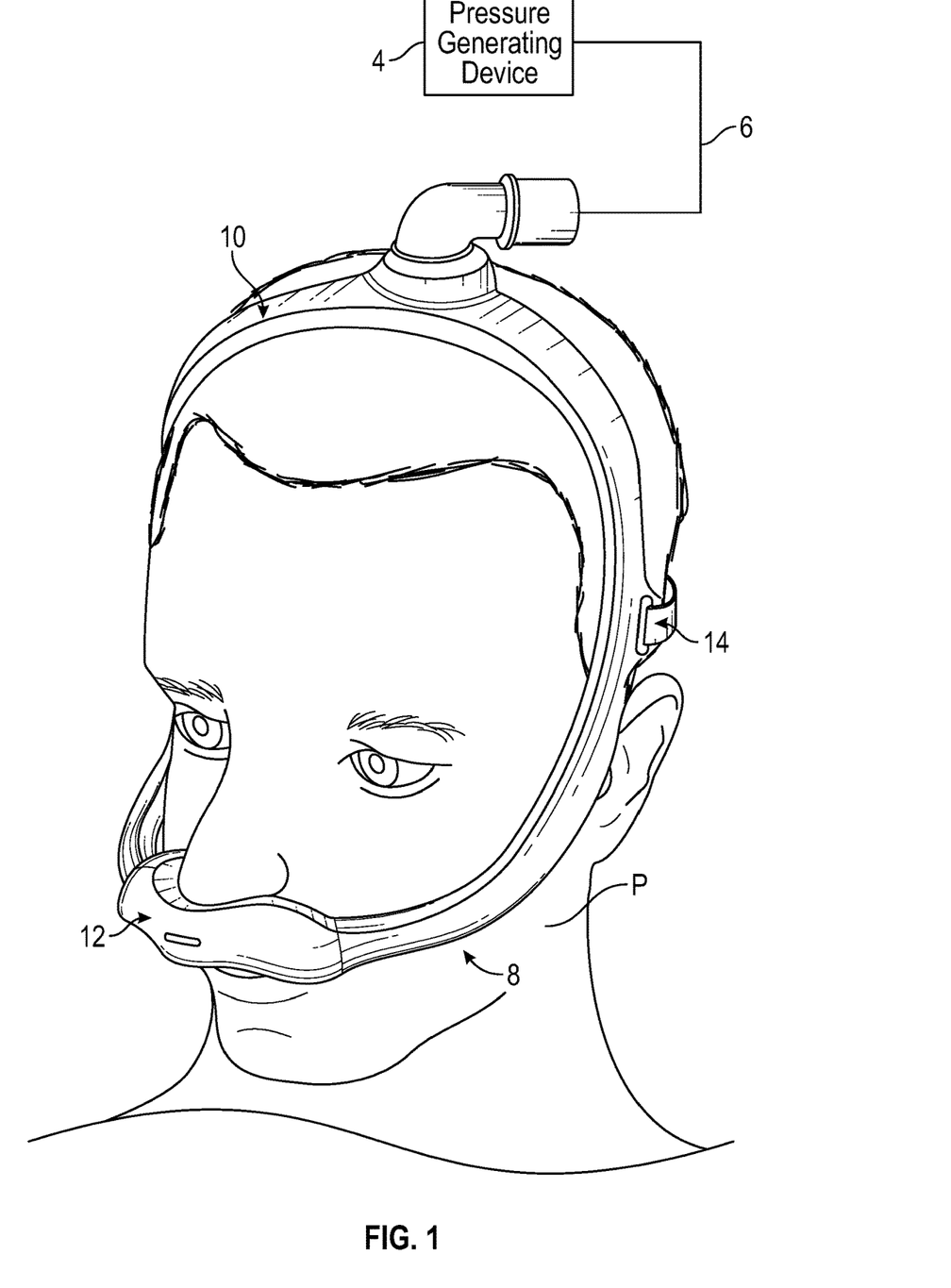
FIG. 1 is a partially schematic depiction of a respiratory interface system for use in providing a flow of positive pressure breathing gas to the airway of a patient in accordance with one example embodiment of the present invention, shown with a patient interface device thereof disposed on the head of a patient and secured thereto by a headgear having an adjustment system in accordance with one example embedment of the present invention.

A respiratory interface system 2 adapted to provide a regimen of respiratory therapy to a patient P according to one exemplary embodiment of the present invention is shown in FIG. 1. Respiratory interface system 2 includes a pressure generating device 4 (shown schematically), and a delivery conduit 6 (shown schematically) fluidly coupled to a patient interface device 8. Pressure generating device 4 is structured to generate a flow of positive pressure breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, PA), and auto-titration pressure support devices. Delivery conduit 6 is structured to communicate the flow of breathing gas from pressure generating device 4 to patient interface device 8, and patient interface device 8 is structured to further communicate the flow of breathing gas received from conduit 6 to an airway of patient P. Delivery conduit 6 and patient interface device 8 are often collectively referred to as a patient circuit. Patient interface device 8 includes a tubing assembly 10 and a mask 12 fluidly coupled to tubing assembly 10. It is to be appreciated that patient interface device 8 and components thereof are provided for example purposes only and that embodiments of the present invention may be readily employed with various other patient interface devices without varying from the scope of the present invention.

Figure 2:
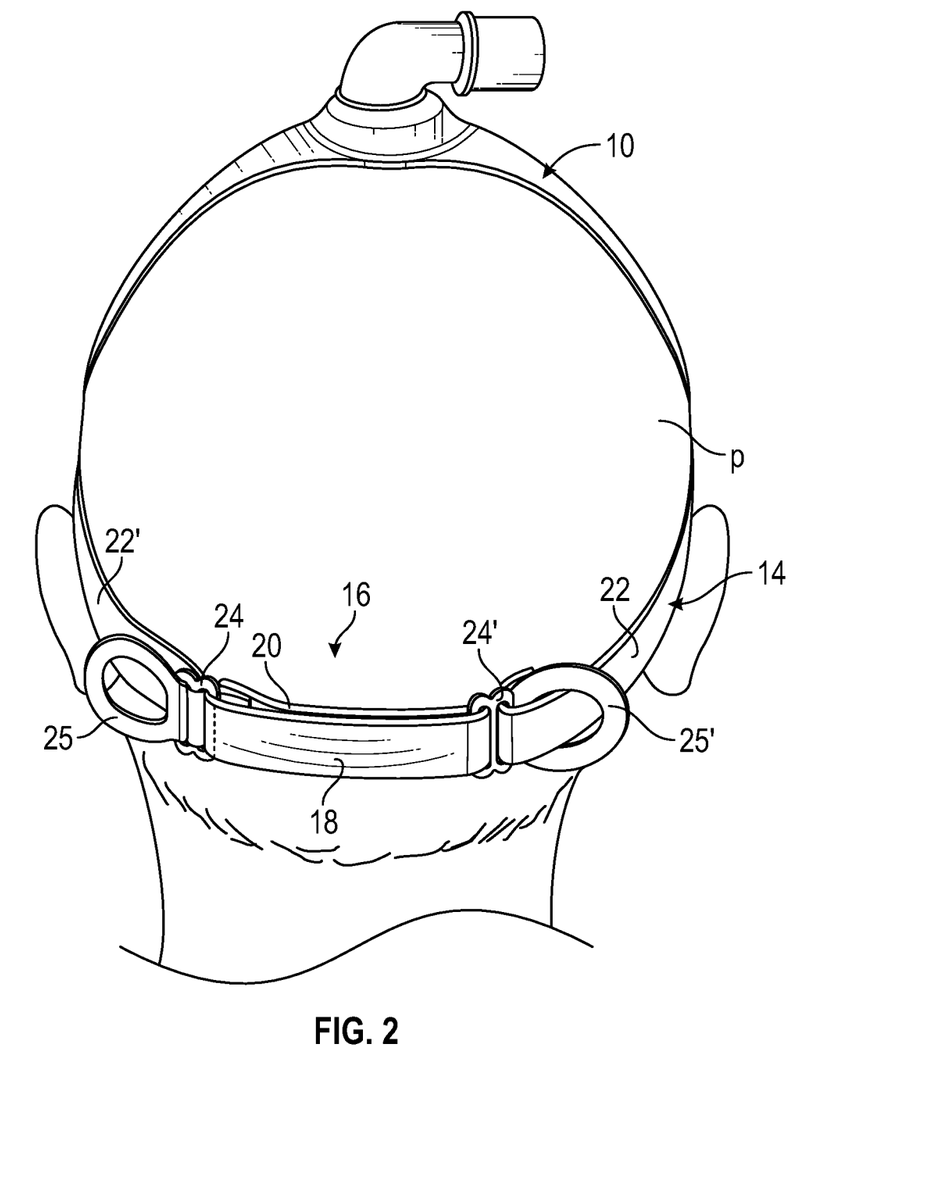
FIG. 2 is rear view of the head of the patient of FIG. 1 with the patient interface disposed on the head of the patient showing the headgear.

Continuing to refer to FIG. 1, as well as to FIG. 2, patient interface device 8 is generally secured to the head of patient P via a headgear 14 having an adjustment system 16 (FIG. 2) in accordance with one example embodiment of the present invention. In the one example embodiment shown in FIGS. 1 and 2, headgear 14 is coupled to patient interface device 8 at two different locations (not numbered) along tubing assembly 10 on different sides of the head of patient P, however, it is to be appreciated that adjustment system 16 may be utilized in various other headgear arrangements without varying from the scope of the present invention.

Figure 3A:
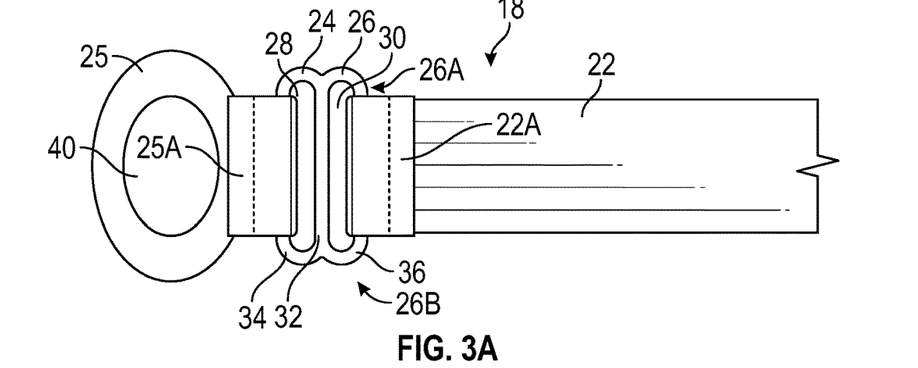
FIGS. 3A-3D are elevation views of strap assemblies of adjustment systems in accordance with some example embodiments of the present invention.
Figure 4:
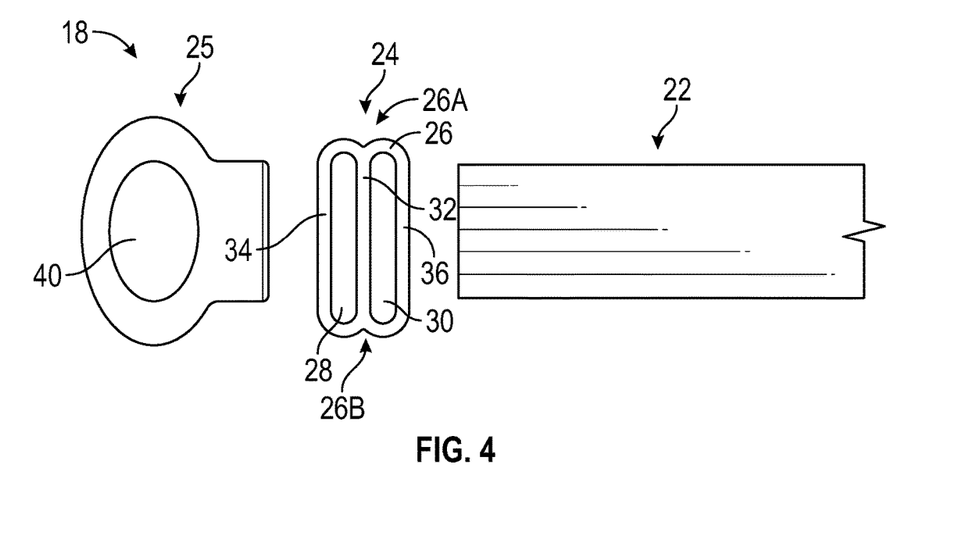
FIG. 4 is an exploded view of the strap assembly of FIG. 3A.

Continuing to refer to FIG. 2, adjustment system 16 includes a first strap assembly 18 and a second strap assembly 20 entwined with each other, as discussed in detail further below. As shown in FIGS. 3A and 4, first strap assembly 18 includes a strap portion 22, a slider 24, and a tab 25 that are coupled together in series such that strap portion 22 and tab 25 are not directly coupled together but instead are coupled together indirectly via slider 24. Such coupling of strap portion 22, slider 24 and tab 25 is discussed in greater detail below.

Strap portion 22 is an elongate, generally thin element formed from a highly flexible material, e.g., without limitation, knit or woven fabrics, laminate materials, or any other suitable material or combination of materials.

Slider 24 includes a body 26 generally of a planar shape that is formed from a rigid material (e.g., coated metal, plastic) or a semi-rigid material (e.g., stiff thermoplastic elastomer). Slider 24 includes a first slot 28 and a second slot 30 defined parallel to each other in body 26. More particularly, first and second slots 28 and 30 are each defined in-part by an elongate central portion 32 of body 26 that is disposed between, and extends along the length of both first slot 28 and second slot 30. First slot 28 is further defined by an elongate first end portion 34 of body 26 that extends along the length of first slot 28 and is disposed parallel to central portion 32. Second slot 30 is further defined by an elongate second end portion 36 of body 26 that extends along the length of second slot 30 and is disposed parallel to central portion 32 on the opposite side thereof from first end portion 34. Central portion 32, first end portion 34, and second end portion 36 are coupled together at a top end 26A of body 26 and at a bottom end 26B via other portions (not numbered) of body 26, thus forming first and second slots 28 and 30.

Tab 25 is structured to be grasped by patient P for use in adjusting adjustment system 16. Tab 25 may be formed from a wide variety of materials without varying from the scope of the present invention. In embodiments in accordance with some examples of the present invention, tab 25 has been formed from non-stretch woven or knit materials (e.g., nylon), flexible polymers (e.g., TPE, silicone, rubber), as well as very thin (e.g., less than 1 mm thickness) rigid polymers (e.g., PP, PC). In the one example shown in FIGS. 2 and 3A, tab 25 includes a large opening 40 defined therein, the purpose of which is described further below.

Referring now to FIGS. 3A-3D, some examples of how strap portion 22, slide 24 and tab 26 may be coupled will be described. In the one example first strap assembly 18 shown in FIG. 3A, strap portion 22 is coupled to slider 24 via an end portion 22A of strap portion 22 that extends through second slot 30 of slider 24 and is folded around second end portion 36 of body 26 back onto the adjacent part of strap portion 22. End portion 22A is secured back onto strap portion 22 via stitching or any other suitable arrangement. Similarly, an end portion 25A of tab 25 is coupled to slider 24 via an end portion 25A of tab 25 that extends through first slot 28 of slider 24 and is folded around first end portion 34 of body 26 back onto the adjacent part of tab 25. End portion 25A is secured back onto tab 25 via stitching or any other suitable arrangement.

Figure 3B:
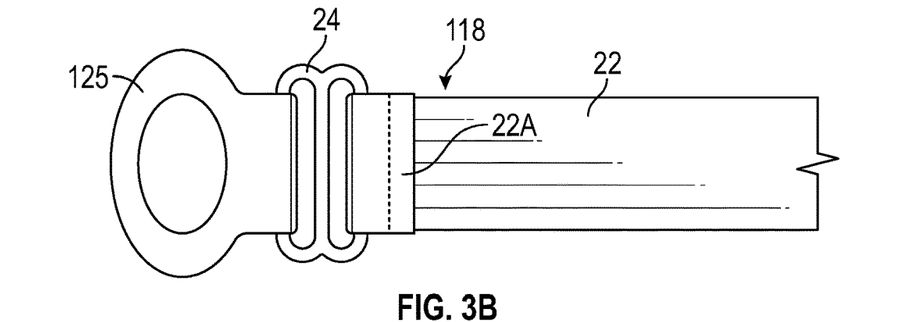

FIG. 3B shows a first strap assembly 118 in accordance with one example embodiment of the present invention in which strap portion 22 is coupled to slider 24 in the same manner as the arrangement of FIG. 3A, however, tab 125 is coupled to slider 24 via over-molding of the tab 125 onto slider 24.

Figure 3C:
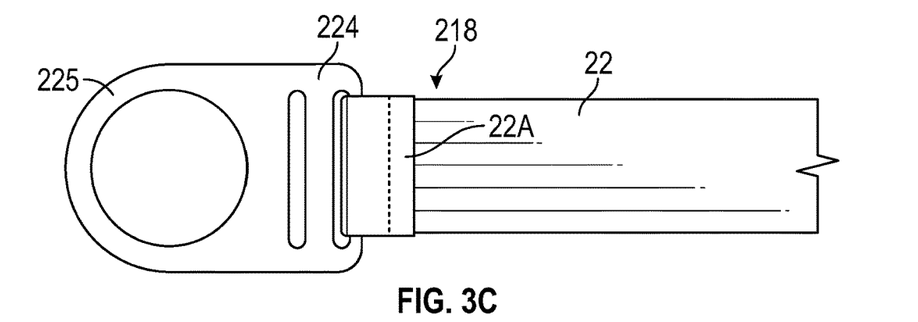

FIG. 3C shows a first strap assembly 218 in accordance with one example embodiment of the present invention in which a tab 225 and a slider 224 are formed as portions of a single unitary member and thus are coupled by virtue of them being formed together. In such example, strap portion 22 is coupled to slider 224 thereof in the same manner as the arrangements of FIGS. 3A and 3B.

Figure 3D:
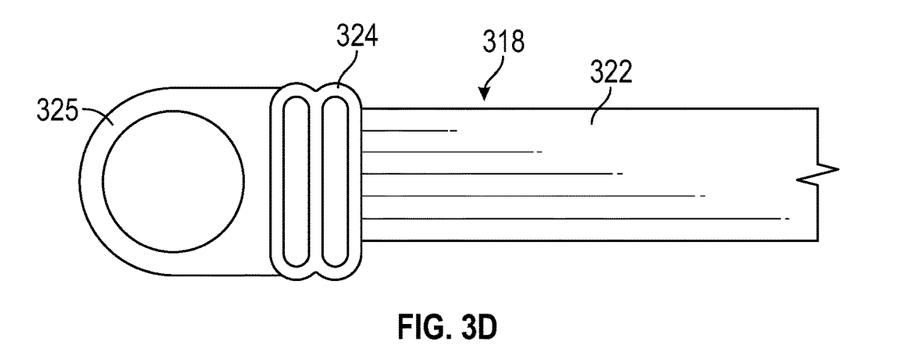

FIG. 3D shows an example first strap assembly 318 in accordance with one example embodiment of the present invention in which a tab 325 is coupled to a strap portion 322 via a slider 324 which is over-molded onto both of tab 325 and strap portion 322.

Figures 5A, 5B, 5C:
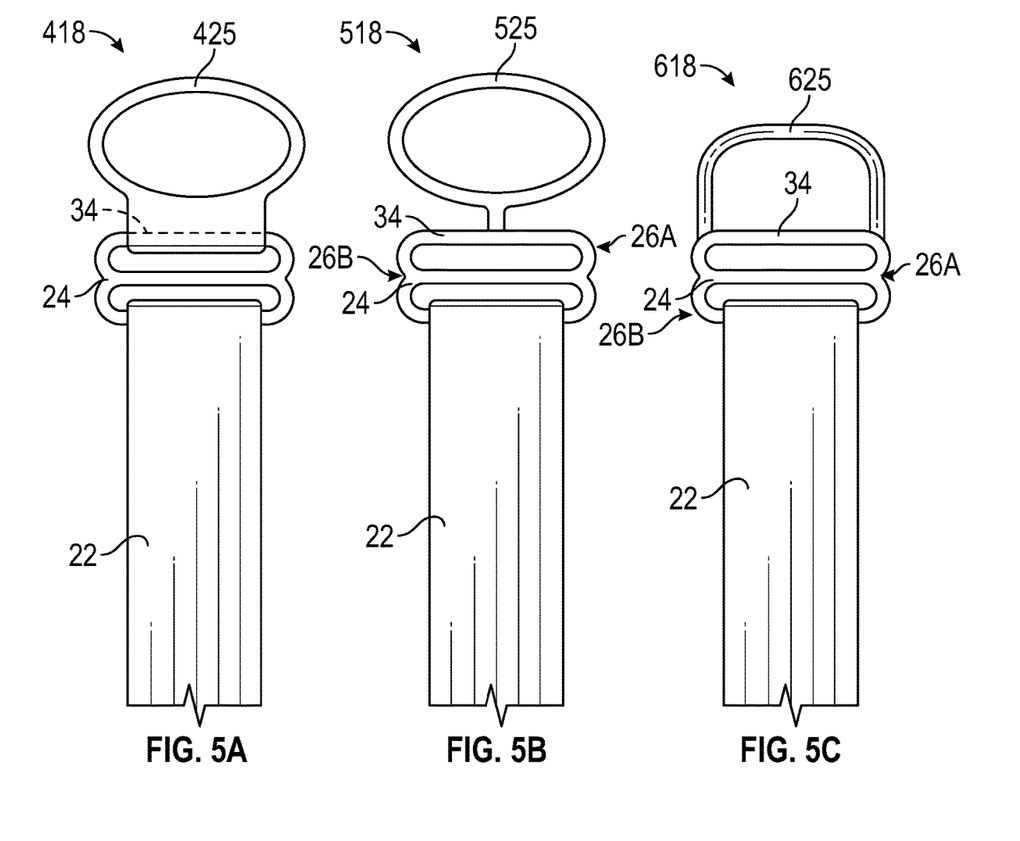
FIGS. 5A-5C are views of strap assemblies of adjustment systems in accordance with some example embodiments of the present invention.

In addition to there being multiple ways in which the tab and slider components of a strap assembly may be coupled, there is also multiple ways in which the tab may engage the slider in a strap assembly. For example, FIG. 5A shows a strap assembly 418 in accordance with one example embodiment of the present invention wherein a tab 425 engages slider 24 along generally the entirety of first end portion 34 thereof. As another example, FIG. 5B shows a strap assembly 518 in accordance with one example embodiment of the present invention wherein a tab 525 engages slider 24 only at a central area of first end portion 34 thereof away from top and bottom ends 26A and 26B thereof. As yet another example, FIG. 5C shows a strap assembly 618 in accordance with one example embodiment of the present invention wherein a tab 625 engages slider 24 only at distal ends of first end portion 34 thereof near top and bottom ends 26A and 26B thereof.

Second strap assembly 20 is of the same arrangement as first strap assembly 18 and thus the description thereof will not be repeated herein. However, in the description of adjustment system 16 that follows, elements of second strap assembly 20 are referred to by the same reference numerals as first strap assembly 18, previously discussed, however, such reference numerals for second strap assembly 20 include prime added thereto. For example, the strap portion of first strap assembly 18 is identified by reference numeral "22", while the strap portion of second strap assembly 20 is identified by reference numeral "22'".

Figure 6:
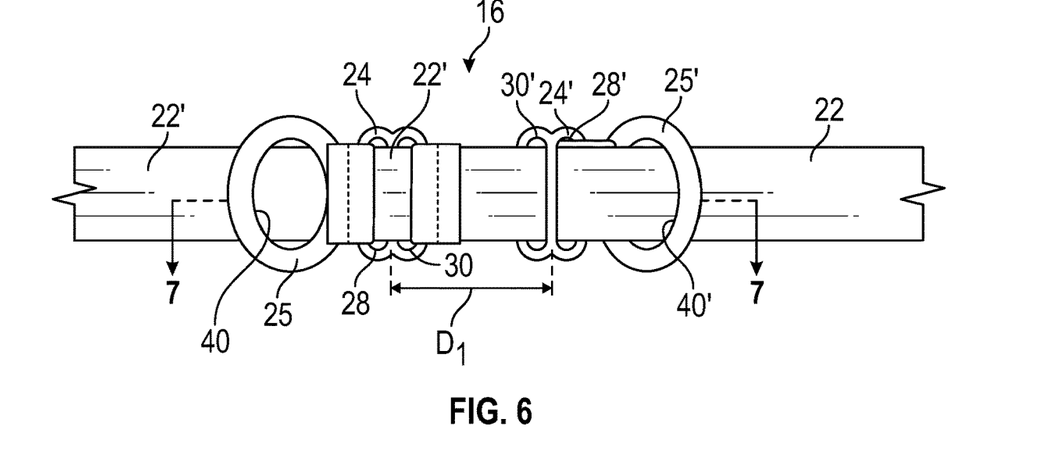
FIG. 6 is a front elevation view of two of the strap assemblies of FIG. 3A shown interlaced forming an adjustment system in accordance with one example embodiment of the present invention.
Figure 7:
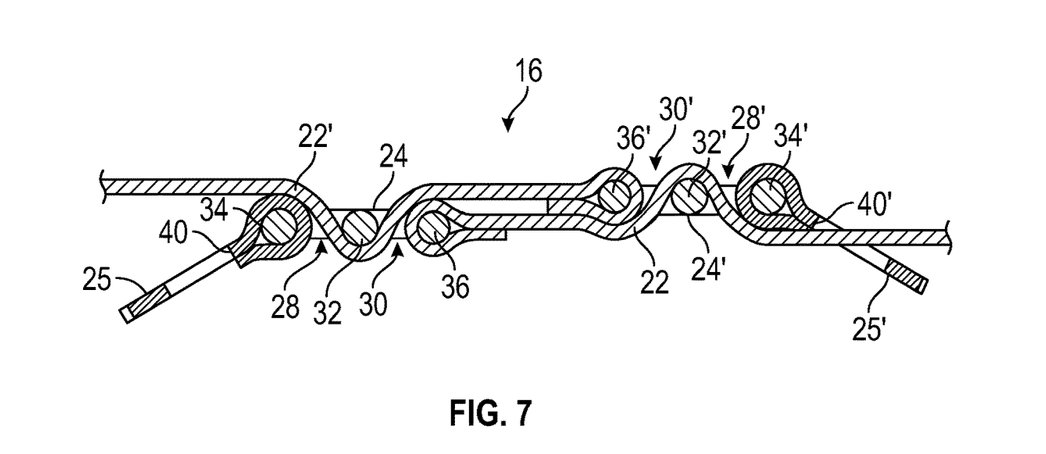
FIG. 7 is a sectional view of the adjustment system of FIG. 6 taken along line 7-7 of FIG. 6.
Figure 8:
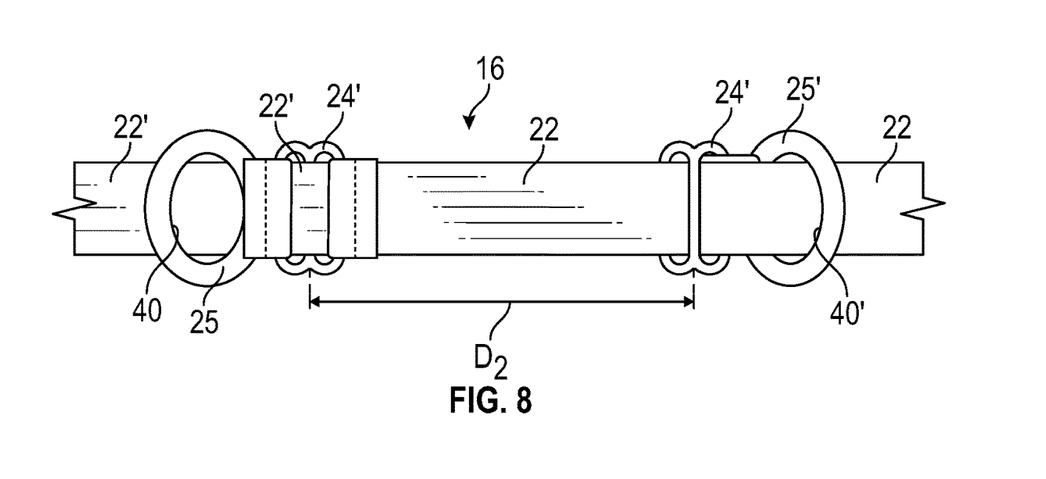
FIG. 8 is another front elevation view of the adjustment system of FIG. 6 shown with the relative positioning of the two strap assemblies adjusted to a second positioning corresponding to a tightening of the adjustment system.

Referring now to FIGS. 6-8, adjustment system 16 will now be described. As previously discussed, adjustment system 16 includes first strap assembly 18 and second strap assembly 20. First strap assembly 18 and second strap assembly 20 are positioned 180 degrees with respect to each other and entwined with each other. More particularly, first and second strap assemblies 18 and 20 are arranged such that strap portion 22 of first strap assembly 18 extends (to the right in FIGS. 6 and 7) from slider 24, along (in front of) strap portion 22' of second strap assembly 20 before passing in front of second end portion 36' of slider 24' of second strap assembly 20. Strap portion 18 then passes rearward through second slot 30' of slider 24', wraps partially around central portion 32' of slider 24', and then passes forward through first slot 28' of slider 24'. Strap portion 22 then passes in front of first end portion 34' of slider 24', passes rearward through opening 40' of tab 25', and then extends to a connection with patient interface device 8. Similarly, strap portion 22' of second strap assembly 20 extends (to the left in FIGS. 6 and 7) from slider 24, along (behind) strap portion 22 of first strap assembly 18 before passing behind second end portion 36 of slider 24 of first strap assembly 20. Strap portion 22' then passes forward through second slot 30 of slider 24, wraps partially around central portion 32 of slider 24, and then passes rearward through first slot 28 of slider 24. Strap portion 22' then passes behind first end portion 34 of slider 24, behind tab 25 (without passing through opening 40), and then extends to another connection with patient interface device 8.

In the one example embodiment shown in FIGS. 2, 6 and 8, adjustment system 16 provides for headgear 14 to be readily tightened to secure patient interface device 8 to the head of patient P. Such adjustment is accomplished simply by grasping each of tabs 25 and 25' and pulling them away from each other (i.e., pulling tab 25 to the left and tab 25' to the right in the views shown in FIGS. 2, 6 and 8. For example, starting with first and second trap assemblies 18 and 20 positioned as shown in FIG. 6, the centers of sliders 24 and 24' are spaced a distance $D_1$. FIG. 8 shows a second positioning of first and second strap assemblies 18 and 20 after tabs 25 and 25' have been pulled away from each other, thus causing sliders 24 and 24' to thus be separated by a second distance $D_2$, which thus reduces the overall length of adjustment system 16 by the length $D_2$-$D_1$. To return first and second strap assemblies 18 and 20 back to the positioning of FIG. 6, a user grasps the top and bottom ends 26A and 26B of each slider 24 and 24' and urges sliders 24 and 24' toward each other, thus loosening headgear 14.

It is to be appreciated that embodiments of the present invention provide for adjustment systems that allow for the use of materials other than laminated un-broken loop fabric/Velcro. For example, without limitation, athletic knits may be employed while still having the ability to adjust. It is also to be appreciated that an adjustment system such as described herein is symmetric, and thus tightens evenly, as opposed to pulling to one side. The large grip pull tabs are easily grasped, and the openings defined therein are easily gripped by at least one finger of a user. The redundant sliders provide for less of a chance for the adjustment to slip. The symmetric design is economically efficient for manufacturing.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An adjustment system for use in a headgear for securing a patient interface device to the head of a patient, the adjustment system comprising:
   (a) a first strap assembly; and
   (b) a second strap assembly positioned 180 degrees with respect to the first assembly and entwined with the first strap assembly, wherein each of the first strap assembly and the second strap assembly comprises:
      (1) a slider having a body formed from a rigid or semi-rigid material, the body comprising:
         (i) a first slot defined in the body; and
         (ii) a second slot defined in the body parallel to the first slot,
         wherein the first slot and the second slot are each defined in-part by an elongate central portion of the body that is disposed between, and extends along the length of both the first slot and the second slot,
         wherein the first slot is further defined by an elongate first end portion of the body that extends along the length of the first slot and is disposed parallel to the central portion,
         wherein the second slot is further defined by an elongate second end portion of the body that extends along the length of the second slot and is disposed parallel to the central portion on the opposite side thereof from the first end portion,
         wherein the central portion, the first end portion, and the second end portion are coupled together at a top end of the body and at a bottom end of the body via other portions of the body, thus forming the first slot and the second slot;
      (2) a strap portion formed from a flexible material, the strap portion having a first end coupled to the second end portion of the slider and an opposite second end structured to be coupled to one or more of the patient interface device or another portion of the headgear; and
      (3) a tab coupled to the first end portion of the slider, the tab being structured to be grasped by the patient
   wherein in each of the first strap assembly and the second strap assembly, the tab is coupled to the first end portion of the slider by an end portion of the tab that:
   extends through the first slot of the slider,
   is folded around the first end portion of the body back onto an adjacent part of the tab, and
   is secured to the adjacent portion of the tab.

2. The adjustment system of claim 1, wherein the tab of each of the first strap assembly and the second strap assembly comprises an opening defined therein.

3. The adjustment system of claim 2, wherein the first strap assembly and the second strap assembly are entwined such that:
   the strap portion of the first strap assembly extends from the slider of the first strap assembly, along the strap portion of the second strap assembly before passing in front of the second end portion of the slider of the second strap assembly;
   the strap portion of the first strap assembly then passes rearward through the second slot of the slider of the second strap assembly, wraps partially around the central portion of the slider of the second strap assembly, and then passes forward through the first slot of the slider of the second strap assembly;
   the strap portion of the first strap assembly then passes in front of the first end portion of the slider of the second strap assembly, passes rearward through the opening of the tab of the second strap assembly, and then extends to an end structured to be coupled with the one or more of the patient interface device or another portion of the headgear;
   the strap portion of the second strap assembly extends from the slider of the second strap assembly, along the strap portion of the first strap assembly before passing behind the second end portion of the slider of the first strap assembly;
   the strap portion of the second strap assembly then passes forward through the second slot of the slider of the first strap assembly, wraps partially around the central portion of the slider of the first strap assembly, and then passes rearward through the first slot of the slider of the first strap assembly; and
   the strap portion of the second strap assembly then passes behind the first end portion of the slider of the first strap assembly, behind the tab of the first strap assembly without passing through the opening of the first strap assembly, and then extends to another end structured to be coupled with the one or more of the patient interface device or another portion of the headgear.

4. The adjustment system of claim 1, wherein in each of the first strap assembly and the second strap assembly, the tab is coupled to the slider via over-molding of a portion of the tab over a portion of the slider.

5. The adjustment system of claim 1, wherein in each of the first strap assembly and the second strap assembly the tab and the slider are formed as portions of a single unitary member.

6. The adjustment system of claim 1, wherein in each of the first strap assembly and the second strap assembly the slider is coupled to the tab via over-molding of a portion of the slider over a portion of the tab and over-molding of another portion of the slider over a portion of the strap portion.

7. A respiratory interface system for providing a regimen of respiratory therapy to a patient comprises:
(a) a patient interface device structured to communicate a flow of breathing gas received to an airway of the patient; and
(b) a headgear coupled to the patient interface device, the headgear structured to secure the patient interface device to the head of the patient, the headgear including an adjustment system comprising:
(1) a first strap assembly; and
(2) a second strap assembly positioned 180 degrees with respect to the first assembly and entwined with the first strap assembly,
wherein each of the first strap assembly and the second strap assembly comprises:
a slider having a body formed from a rigid or semi-rigid material, the body comprising:
(i) a first slot defined in the body; and
(ii) a second slot defined in the body parallel to the first slot,
wherein the slot and the second slot are each defined in-part by an elongate central portion of the body that is disposed between, and extends along the length of both the first slot and the second slot,
wherein the first slot is further defined by an elongate first end portion of the body that extends along the length of the first slot and is disposed parallel to the central portion,
wherein the second slot is further defined by an elongate second end portion of the body that extends along the length of the second slot and is disposed parallel to the central portion on the opposite side thereof from the first end portion,
wherein the central portion, the first end portion, and the second end portion are coupled together at a top end of the body and at a bottom end of the body via other portions of the body, thus forming the first slot and the second slot;
(iii) a strap portion formed from a flexible material, the strap portion having a first end coupled to the second end portion of the slider and an opposite second end structured to be coupled to one or more of the patient interface device or another portion of the headgear; and (iv) a tab coupled to the first end portion of the slider, the tab being structured to be grasped by the patient
wherein in each of the first strap assembly and the second strap assembly, the tab is coupled to the first end portion of the slider by an end portion of the tab that:
extends through the first slot of the slider,
is folded around the first end portion of the body back onto an adjacent part of the tab, and
is secured to the adjacent portion of the tab.

8. The respiratory interface system of claim 7, further comprising:
a pressure generating device structured to generate the flow of breathing gas; and
a delivery conduit fluidly coupled between the pressure generating device and the patient interface device, the delivery conduit structured to communicate the flow of breathing gas from the pressure generating device to the patient interface device.

9. The respiratory interface system of claim 7, wherein the tab of each of the first strap assembly and the second strap assembly comprises an opening defined therein.

10. The respiratory interface system of claim 9, wherein the first strap assembly and the second strap assembly are entwined such that:
the strap portion of the first strap assembly extends from the slider of the first strap assembly, along the strap portion of the second strap assembly before passing in front of the second end portion of the slider of the second strap assembly;
the strap portion of the first strap assembly then passes rearward through the second slot of the slider of the second strap assembly, wraps partially around the central portion of the slider of the second strap assembly, and then passes forward through the first slot of the slider of the second strap assembly;
the strap portion of the first strap assembly then passes in front of the first end portion of the slider of the second strap assembly, passes rearward through the opening of the tab of the second strap assembly, and then extends to an end structured to be coupled with the one or more of the patient interface device or another portion of the headgear;
the strap portion of the second strap assembly extends from the slider of the second strap assembly, along the strap portion of the first strap assembly before passing behind the second end portion of the slider of the first strap assembly;
the strap portion of the second strap assembly then passes forward through the second slot of the slider of the first strap assembly, wraps partially around the central portion of the slider of the first strap assembly, and then passes rearward through the first slot of the slider of the first strap assembly;
the strap portion of the second strap assembly then passes behind the first end portion of the slider of the first strap assembly, behind the tab of the first strap assembly without passing through the opening of the first strap assembly, and then extends to another end structured to be coupled with the one or more of the patient interface device or another portion of the headgear.

* * * * *